United States Patent [19]
Juergens

[11] Patent Number: 5,889,049
[45] Date of Patent: Mar. 30, 1999

[54] USE OF TERPENE COMPOUNDS FOR REDUCED RELEASE OF ARACHIDONIC ACID AND OF INFLAMMATION MEDIATORS

[76] Inventor: Uwe R. Juergens, Rheinallee 2, D-53859 Niederkassel, Germany

[21] Appl. No.: 373,294

[22] PCT Filed: Jun. 11, 1994

[86] PCT No.: PCT/EP94/01900

§ 371 Date: Feb. 23, 1995

§ 102(e) Date: Feb. 23, 1995

[87] PCT Pub. No.: WO94/28895

PCT Pub. Date: Dec. 22, 1994

[30] Foreign Application Priority Data

Jun. 13, 1993 [DE] Germany ............... 43 19 556.3
Jun. 13, 1993 [DE] Germany ............... 43 19 554.7

[51] Int. Cl.[6] ............ A61K 31/045; A61K 31/075; A61K 31/095; A61K 31/12
[52] U.S. Cl. ............ 514/510; 424/451; 514/691; 514/729; 514/962
[58] Field of Search ............ 424/451; 514/510, 514/690, 691, 729, 962; 549/397; 568/829

[56] References Cited

U.S. PATENT DOCUMENTS

| | | | |
|---|---|---|---|
| 4,103,019 | 7/1978 | Mira | 548/528 |
| 4,775,667 | 10/1988 | Saitoh et al. | 514/160 |
| 5,120,538 | 6/1992 | Oei | 424/195.1 |
| 5,294,443 | 3/1994 | Lipsky et al. | 424/195.1 |
| 5,322,689 | 6/1994 | Hughes et al. | 424/401 |
| 5,338,758 | 8/1994 | Chu et al. | 514/468 |
| 5,420,162 | 5/1995 | Blumberg et al. | 514/570 |
| 5,464,754 | 11/1995 | Dennis et al. | 435/18 |
| 5,527,890 | 6/1996 | Rao et al. | 536/5 |
| 5,580,562 | 12/1996 | Lipsky et al. | 424/195.1 |
| 5,616,458 | 4/1997 | Lipsky et al. | 435/4 |
| 5,665,386 | 9/1997 | Benet et al. | 424/451 |

FOREIGN PATENT DOCUMENTS

4211745-A1 10/1993 Germany.
4-26619 1/1992 Japan.

OTHER PUBLICATIONS

Cousergue, J.L., Allergies to Terpene Products in Asthmaties., Revue Francese D'Allergolgie 5, 3 Jul.–Sep. 1965, pp. 160–168 (Full Translated Copy).

Cousergue, J.L. Allergy to Terpene Products in Asthmatic Subjects (Occupational Allergies Excluded). Moroccan Study. Rev–Fr–Allergol. vol. 5, No. 3, pp. 160–168 (1965). Full Translation.

Wagner, H., et al. in–Vitro Inhibition of Prostaglandin Biosynthesis by Essential Oils and Phenolic Compounds. Planta Medica. No. 3, pp. 184–187. 1986. Full Translation.

Grimm, H. Antiobstruktive Wirksamkeit von Cineol Bei Atemwegserkrankungen. Therapiewoche, vol. 37, No. 45, pp. 4306–4311. (1987). Full Translation.

Flower, R.J., et al. Anti–inflammatory Steroids Induce Biosynthesis of Phospholipase A2 Inhibitor Which Prevents Prostaglandin Generation. Nature, vol. 278, pp. 456–459. 29 Mar. 1979.

Fisher, D.A. Exercise–Induced Bronchoconstriction Related to Isotretinoin Therapy. J–Am–Acad–Dermatol. vol. 13, No. 3, p. 524. Sep. 1985.

(List continued on next page.)

*Primary Examiner*—Robert H. Harrison
*Attorney, Agent, or Firm*—Cohen, Pontani, Lieberman & Pavane

[57] ABSTRACT

Disclosed is a method of treatment of steroid requiring inflammatory diseases using certain saturated monocyclic and bicyclic terpene compounds. These compounds may be administered in the form of capsules resistant to gastric juice, infusion solutions or intramuscular injection solutions. Because these particular terpene compounds exhibit steroid-like effects but without the harmful side-effects of conventional corticosteroids, the use of corticosteroids is substantially reduced, and in some cases, completely eliminated. Therefore, these terpene compounds are also suitable for long-term therapy and prophylaxis.

39 Claims, 4 Drawing Sheets

OTHER PUBLICATIONS

Grimm, H. Antiobstruktive Wirksamkeit von Cineol Bei Atemwergekrankungen. Therapiewoche, vol. 37, No. 45, pp. 4306–4311. (1987).

Fiedler–Nagy, C., et al. Comparative Study of Natural and Synthetic Retinoids as Inhibitors of Arachidonic Acid Release and Metabolism in Rat Peritoneal Macrophages. Dermatogica.
Vol. 175: Supplement 1, pp. 81–92. (1987).

Fawzy, A.A., et al. Inhibition Of Human Non–Pancreatic Phospholipases A2 by Retinoids and Flavonoids. Mechanism of Action. Agents & Actions. 25(3–4) pp. 394–400. (1988).

Eccles, R., et al., The Effects of Oral Administration of (–) Menthol on Nasal Resistance to Airflow & Nasal Sensation of Airflow in Subjects Suffering from Nasal Congestion.
Associated with the Common Cold. J. Pharm. Pharmacol., vol. 42, pp. 652–654. (1990).

Hope et al. Retinoids Inhibit Phoapholipase A2 in Human Synovial Fluid and Arachidonic Acid Release From Rat Peritoneal Macrophages. Inflammation, 14(5), pp. 543–549. (1990).

Trampsch, K.M., et al. Novel Inhibitor of Phospholipase A2 With Topical Anti–Inflammatory Activity. Biochemical and Biophysical Research Communications. 189(1) pp. 272–279. Nov. 1992.

USE OF TERPENE COMPOUNDS FOR REDUCED RELEASE OF ARACHIDONIC ACID AND OF INFLAMMATION MEDIATORS

BACKGROUND OF THE INVENTION

The present invention relates to the use of saturated monocyclic or bicyclic terpenes for the treatment of inflammatory diseases. It is particularly concerned with the use of saturated monocyclic terpenes for the treatment of steroid-requiring inflammatory diseases exacerbated by infection, such as, for example, bronchial asthma.

Acute and/or chronic inflammatory or acute allergic and/or chronic allergic inflammatory lesions are characterized by inflammatory infiltration of various organ systems by monocytes/macrophages, eosinophils, basophils and neutrophils, granulocytes, mast cells and thrombocytes. The degree of inflammatory activity correlates with the influence of these inflammatory cells in organ tissue, which causes damage to the organ concerned. These processes are a familiar feature in primary inflammatory diseases of the airways, the intestine and the articular cartilage in rheumatoid arthritis. Since the primary cause triggering most chronic inflammatory diseases is not known, these diseases can only be alleviated by nonspecific suppression of the inflammation stimulus. In an appropriate genetic predisposition or in the presence of environmental noxae, the reaction of the body to the exogenous noxae can be inhibited prophylactically by nonspecific suppression of the inflammation stimulus before the manifestation of disease symptoms.

At the level of the cell, the further migration of inflammatory cells into an area of inflammation can be reduced by inhibiting chemotactic factors. This leads to the inflammatory activity subsiding with decline of the morphological and functional disorders of the organ system concerned, an effect which is typically mediated by immunosuppressants, e.g. corticosteroids. This group of agents is known to have an activity profile which comprises a strong anti-inflammatory effect, but is only poorly tolerated since it causes severe side effects, namely osteoporosis, gastric and duodenal ulcers, steroid purpura or lymphopenia.

Corticosteroids are known to inhibit the activity of phospholipase and cytokines in various inflammatory cells. After inhibition of the phospholipase activity, the release of arachidonic acid from the phospholipid stores in the cell membrane is inhibited. Arachidonic acid is known to be an important substrate for the formation of various mediators.

The actual inhibitory action on inflammation is mediated by inhibition of cytokine production and via a reduced production of arachidonic acid. The latter is the precursor for the formation of potent chemotactic metabolites of the 5-lipoxygenase pathway (leukotrienes) and the cyclooxygenase pathway (prostaglandins, thromboxane) with a constrictor action on smooth muscle cells. Owing to the persistent suppression, especially of mediators of the 5-lipoxygenase metabolic pathway, the need for systemically active corticosteroids is therefore reduced and the activity of the inflammatory process is suppressed with diminishing infiltration with inflammatory cells.

For this reason, the disease course of various acute, chronic or allergic inflammations can be favorably influenced by nonspecific inhibition of inflammation.

SUMMARY OF THE INVENTION

The subject matter of the present invention is the use of saturated monocyclic or bicyclic terpenes, especially those of a menthane, terpene alcohol, thiol, ketone or carane, pinane, bornane basic structure or a corresponding oxo compound of the bicyclic terpene structures (1,8-oxidomenthane and menthol are especially preferred) for suppression of the release of arachidonic acid, mediators of inflammation and cytokines.

DETAILED DESCRIPTION OF THE PRESENTLY PREFERRED EMBODIMENTS

Figure 1:
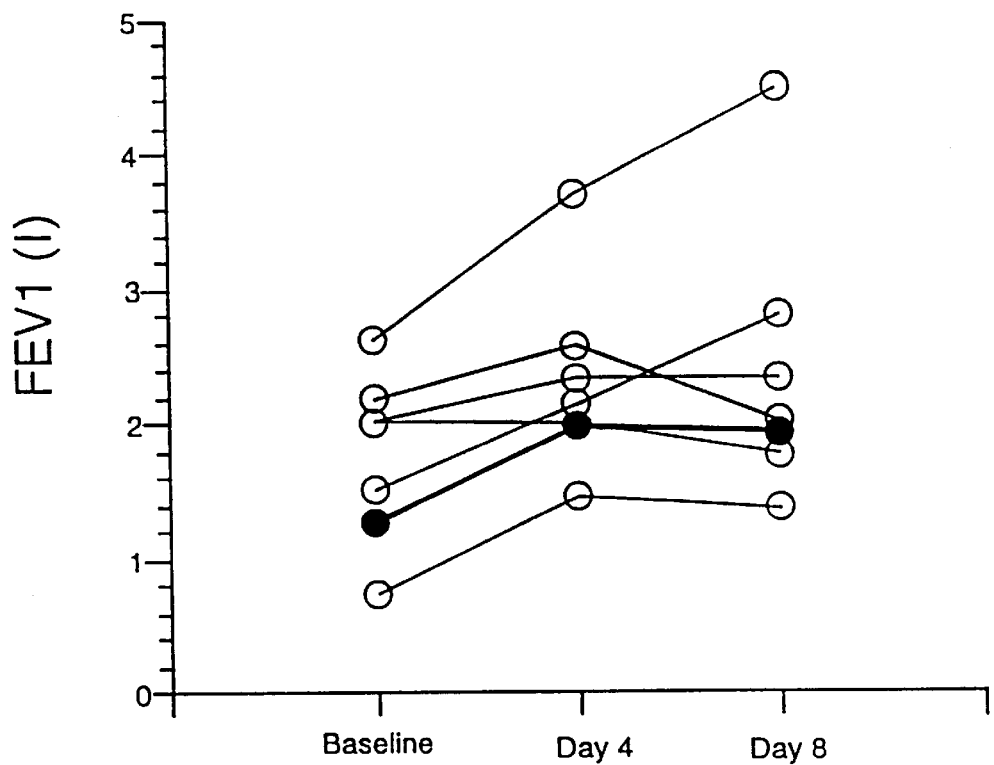
FIG. 1 is a graph showing the effects of cineol on the $FEV_1$ in patients with asthma.

The saturated, monocyclic and bicyclic terpene structures which can be used in accordance with the invention include inter alia monocyclic terpenes of the menthol type ((-)menthane-3-ol) and the eight stereoisomers as well as 1,8-terpin, menthone (p-menthane-3-one) as examples of terpene alcohols and terpene ketones as well as terpene thiols and the bicyclic terpenes. These include 1,8-cineol, carane, pinane, bornane and their oxo derivatives carone, camphor, borneol and the respective stereoisomers. They are suitable for treating allergic inflammatory or inflammatory bronchopulmonary diseases requiring steroid treatment and/or which are exacerbated by infections, allergic and chronic rhinitis and sinusitis, interstitial lung diseases with activated alveolar macrophage function, e.g. sarcoidosis, fibrosis, exogenous allergic alveolitis, pneumoconioses, diseases of the efferent biliary tract, especially cholecystitis and cholangitis, diseases of the efferent urinary tract, especially glomerulonephritis, pyelonephritis, cystitis, urethritis as well as inflammatory and allergic skin diseases (especially eczema and psoriasis) and inflammatory arterial and venous vascular diseases including arteriitis, arteriosclerosis and phlebitis.

Surprisingly, it was found that of the group of the terpene structures in accordance with the invention 1,8-cineol is suitable for treating inflammatory allergic and/or inflammatory bronchopulmonary diseases requiring steroid treatment and exacerbated by infection. The group reduces the product of arachidonic acid. In this way, it suppresses arachidonic metabolism in the 5-lipoxygenase pathway. In addition, an inhibition of interleukin 1β ($IL_1$-β) was found. Interleukin 1β conditions human cells to release arachidonic acid and is known to be a strong proinflammation mediator itself. The effects may be attributed to its lipophilic properties, i.e. the diffusion and storage in fat tissue. This results in a new indication for the group of substances which also includes 1,8-cineol, especially for treatment of inflammatory diseases or inflammatory allergic diseases requiring steroid treatment and exacerbated by infection, e.g. bronchopulmonary conditions. For example, the use of corticosteroids can be substantially reduced in consequence of the mode of action of 1,8-cineol. Long-term therapy is therefore recommended.

Because of the synergistic effect, a combination treatment comprising 1,8-cineol and the conventional corticosteroids prednisone, prednisolone, fluocortolone, beclomethasone, budesonide or flunisolide is recommended.

Cineol is the main constituent (about 80%) of the eucalyptus oils of the various kinds of *Eucalyptus globulus* type. 1,8-Oxidomenthane is a bicyclic ether which has a tension-free ring system and is designated 2-oxa-bicyclo/2,2,2/-octane according to IUPAC. It is a colorless fluid, with an aromatic camphorlike smell which is also present in sage, myrtle, eucalyptol and other ethereal oils.

The dosage varies in the saturated monocyclic and bicyclic terpene structures, but is lower than the doses at which adverse side effects or indeed intoxications are manifested. Thus a dosage of 200 mg/day to 900 mg/day (by preference 600 mg/day) can be administered in the form of gastric juice-resistant capsules with a dose unit of 100 mg/capsule. 1,8-cineol and menthol are suitable as additives for long-term intravenous infusion and for intramuscular administration. Cineol and menthol can be combined with other substances.

The dosage of menthol is between 100 mg/day and 450 mg/day. For example, 1,8-cineol is administered for the purposes of the invention at a dosage of 200 mg/day to 900 mg/day (by preference 600 mg/day). The overall amount of the substances mentioned is appropriately divided into three doses per day.

The medical preparation forms can be solid or fluid. In addition, it is possible to administer the active agent with vehicles, diluents and additives which are usual in biopharmaceutics, are pharmacologically harmless and are compatible with 1,8-cineol. Additives include fillers, dispersants, binding agents, moisteners, stabilizers, lubricants, emulsifiers, sweeteners, flavors and similar. These additives include for example Melantine solutions, pectin solutions, lactose, sodium chloride, talcum, starch, boric acid, paraffin oil, paraffin, stearic acid and its derivatives, cocoa butter, rubber, syrups, licorice extracts, yeast extracts, honey, glycerol, silicious earth, kaolin, magnesium oxide, beeswax and plant oils.

In fluid preparation forms, water, glycerol, sugar or alcohol solutions or mixtures of these can be used as vehicle and auxiliary agent. The methods of optimizing the formulation are familiar to the specialist (Chemie in unserer Zeit 23, 114 and 161 (1989)).

The present invention is more particularly described and explained by the following examples. It should be understood, however, that the preferred embodiments and examples described are for illustrative purposes only and are not to be construed as limiting the scope of the present invention which is properly delineated only in the appended claims.

EXAMPLE 1

It was found by in vitro investigations that the effect of cineol is based on the inhibition of arachidonic acid release from the phospholipid stores in almost all human cells. Consequently, only reduced amounts of arachidonic acid (as substrate for 5-lipoxygenase and cyclo-oxygenase metabolic pathway) is available for mediator formation.

In these experiments, a significant suppression of monocyte $LTB_4$ production ex vivo with improvement of lung function could be demonstrated after four days of therapy in patients with allergic and nonallergic bronchial asthma (n=7) (see Tab. I, FIG. 1–4). 50 ml of venous blood were taken from patients with allergic and nonallergic bronchial asthma before therapy, after four days of therapy and four days after discontinuation of cineol administration (day 8).

Monocytes were isolated by means of density gradient centrifugation and purified by further centrifugation. Fifty thousand cells were stimulated in 1 ml of culture supernatant in plastic tubes for 30 minutes with calcium ionophore A23187 in a water bath at 37° C. After incubation, the tubes containing the cells were centrifuged for five minutes at 4° C. and the culture supernatants obtained were stored at −80° C. until further analysis. Afterwards, the culture supernatants were thawed and $LTB_4$ determined with a specific enzyme immunoassay.

Figure 2:
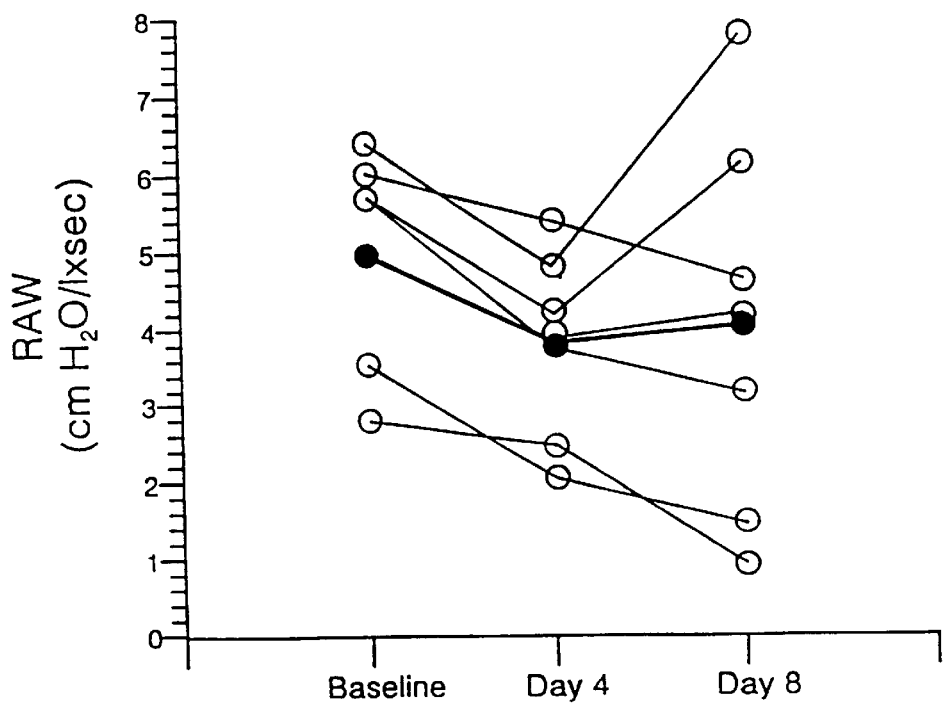
FIG. 2 is a graph showing the effects of cineol on the airway resistance of patients with asthma.
Figure 3:
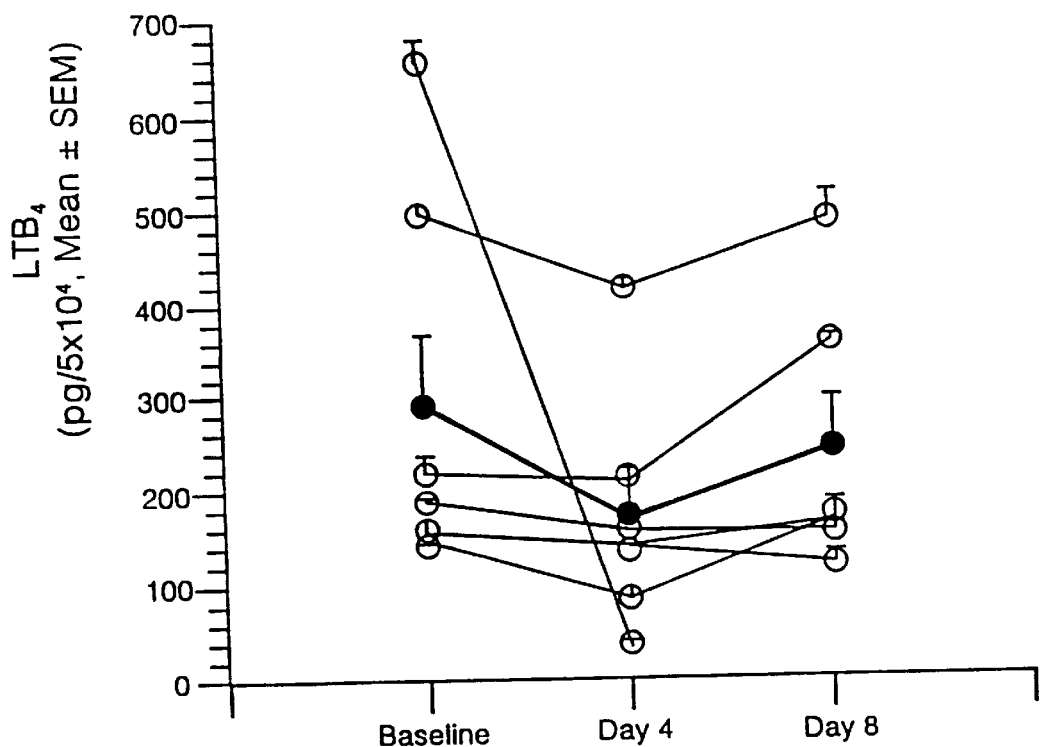
FIGS. 3 and 4 are graphs showing the effects of 1,8-cineol on $LTB_4$ production in patients with asthma in vivo.
Figure 4:
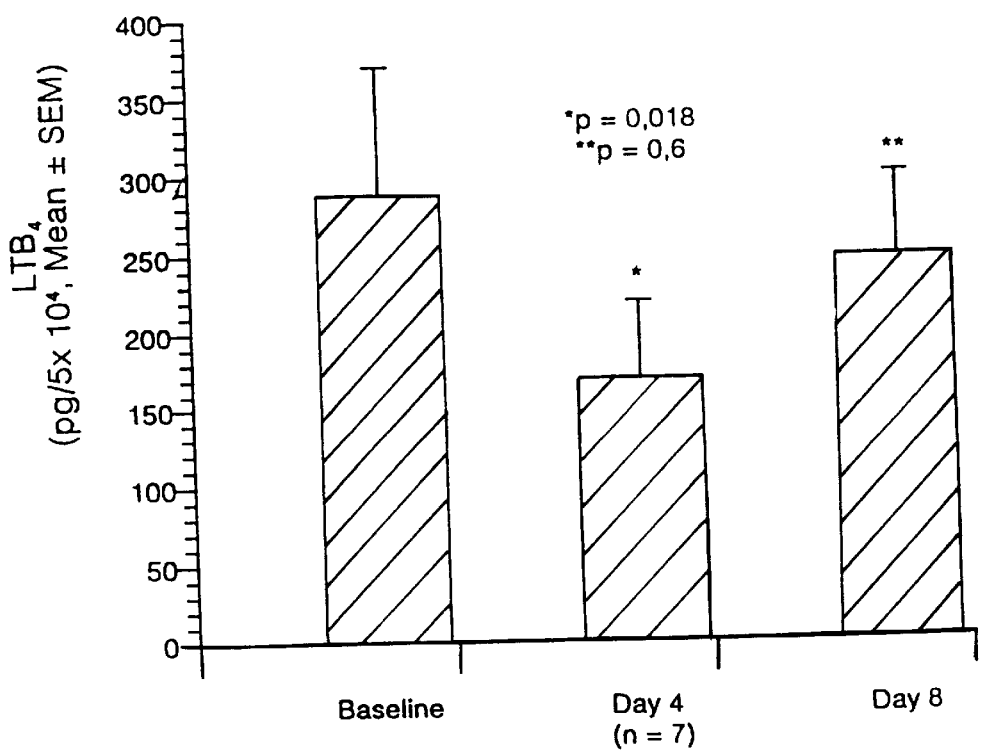

After treating the same seven patients with 3×200 mg cineol in capsules for four days, blood was taken and the same analysis for $LTB_4$ was repeated. The treatment with cineol was then discontinued and the same investigation was repeated after a further four days (day 8). The results are shown in FIGS. 3 and 4: in all cases, cineol brought about a significant decrease of $LTB_4$ production. However, this rose again to the initial value after discontinuation of cineol (day 8). Table I in conjunction with FIGS. 1 and 2 shows the clinical data. $FeV_1$ is the forced one second capacity and RAW is the airway resistance.

Figure 5:
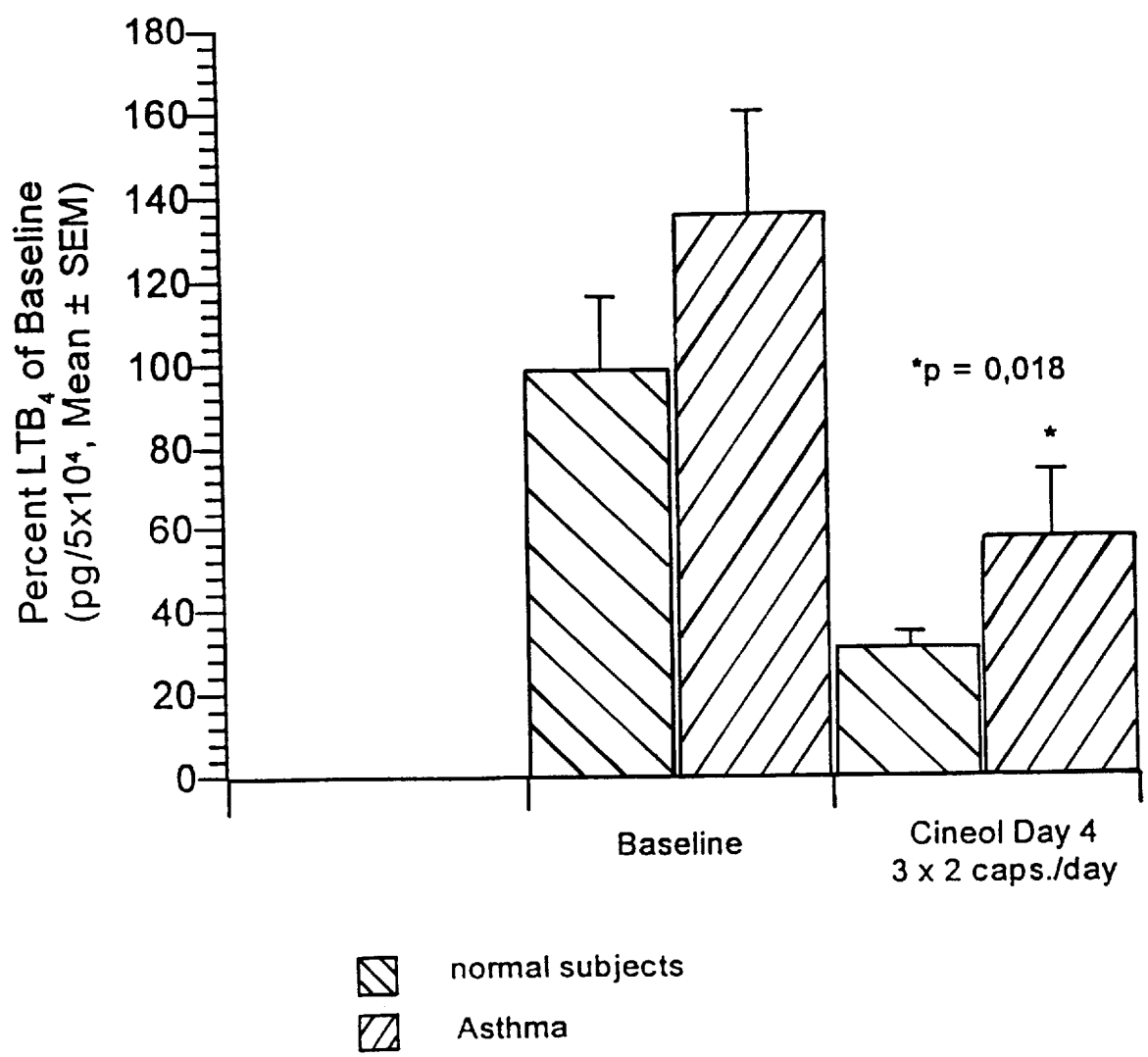
FIG. 5 is a graph showing the inhibition of monocyte $LTB_4$ production in normal subjects and in asthma patients.
Figure 6:
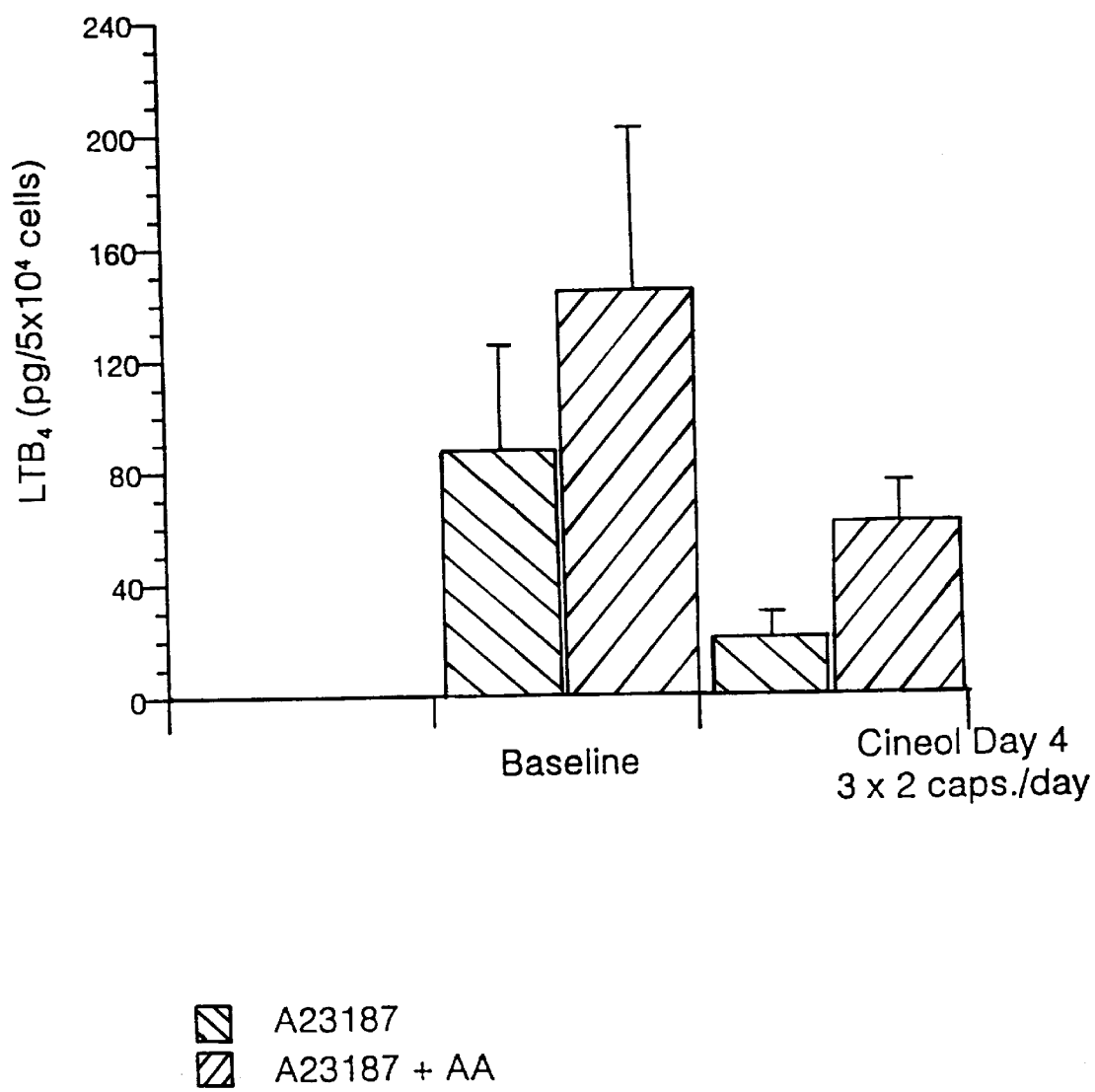
FIG. 6 is a graph showing the inhibition of AA metabolism in normal monocytes by 1,8-cineol.

The $LTB_4$ production in monocytes of seven healthy test subjects (25±2 years) before and after the same cineol treatment was also used for comparison (see FIG. 5). Compared to patients with asthma, the $LTB_4$ production had also fallen in healthy patients, so that a general effect must be assumed. FIG. 6 shows that cineol alone also inhibits the calcium ionophore A23187-stimulated $LTB_4$ production in monocytes. Consequently, cineol on its own is also suitable for treating inflammatory bronchopulmonary disease exacerbated by infections.

The right columns of FIG. 5 show the unexpected synergistic efficacy of 1,8-cineol in the treatment of bronchial asthma patients in accordance with the invention, because even cortisone treatment could not reduce $LTB_4$ production to normal, whereas simultaneous cineol treatment brings $LTB_4$ production into the normal range, so that cortisone can be saved to an equal extent.

The same was proved by a long-term therapy (43±7 days) of patients with bronchial asthma requiring steroid administration (n=5). These profit from a significant decrease of the steroid requirement and an improvement of lung function under cineol (3×200 mg/day; Tab. II). The A23187 stimulated LTB4 production from monocytes ex vivo also did not rise after reduction of systemic glucocorticosteroid therapy under long-term cineol treatment.

The corticosteroid requirement before cineol averaged 8.9±3.3 mg/day (range 0–24 mg) and could be reduced after 43.5±7.3 days to 4.0±1.3 mg/day (range 0–8 mg/day). The reduction of steroid therapy did not have any negative effect on lung function. The $FeV_1$ before cineol (1.83±0.26 l) rose to 2.7±0.55 l (p=0.0431) after long-term therapy (n=6 test subjects). The resistance before cineol treatment (5.49±1.02 cm $H_2O$/l×sec) had fallen to 3.98±1.2 cm $H_2O$/l×sec after long-term therapy with cineol (p=0.0273). The $LTB_4$ production for cineol had also fallen after long-term therapy. The results of long-term therapy show for the first time that there is a marked decrease in the daily steroid requirement under therapy with cineol without deterioration of lung function. The average $LTB_4$ production under cineol after long-term therapy is markedly suppressed. The reduction of systemic corticosteroids under long-term therapy with cineol only leads to a rise of the $LTB_4$ production in patients who as a result of a high steroid dose had shown suppression of $LTB_4$ production in vitro before cineol administration.

Lipopolysaccharide-(LPS)-stimulated formation of IL1-β from monocytes of healthy subjects (n=4) was determined before taking cineol, after treatment for four days with 3×2 capsules (=3×200 mg cineol/day) and four days after discontinuation of cineol (day 8). In all test subjects investigated, the $IL_1$-$\beta$ production on day 4 and 8 was inhibited by an average of 60%. Since the production of $IL_1$-$\beta$ was still suppressed four days after discontinuation of cineol (=day 8), a strong anti-inflammatory action must be assumed which is very suitable for prophylaxis (e.g. in patients with bronchial asthma and in children) because of the long-term effect.

EXAMPLE 2

Healthy test subjects were treated for four days with 3×150 mg menthol per day p.o. (dose unit=150 mg/capsule). After four days of treatment, the calcium ionophore A23187-stimulated $LTB_4$ production of isolated monocytes was suppressed by up to 75%.

In patients with bronchial asthma, an improvement of lung function could be attained as under cineol treatment after four days of therapy with the above dose. After long-term therapy for 12 weeks, the bronchial asthma stabilized to such an extent that the systemic corticosteroid requirement could be reduced by up to 50%. The treatment was tolerated well without side effects.

I claim:
1. A method of treating a human to inhibit the onset of chronic, acute or allergic inflammatory diseases comprising:
   systemically administering a therapeutically effective amount of a pharmaceutical compound comprising a saturated monocyclic or bicyclic terpene -alcohol, -ether, -ketone, or -thiol,
   thereby suppressing the release of arachidonic acid from the phospholipid stores of human cells, and the production and release of inflammatory mediators and cytokines from human cells.
2. The method defined in claim 1 wherein said saturated monocyclic or bicyclic terpene -alcohol, -ether, -ketone, or -thiol, is administered in solid or fluid form.
3. The method defined in claim 1 wherein said pharmaceutical compound is a menthane compound selected from the group consisting of 1,8-oxido-p-menthane and menthane-3-ol.
4. The method defined in claim 1 wherein said inflammatory diseases are infection-exacerbated or allergic conditions.
5. The method defined in claim 1 wherein said inflammatory diseases are steroid-requiring-acute allergic or chronic bronchopulmonary conditions.
6. The method defined in claim 1, wherein said inflammatory diseases are inflammatory conditions of the upper and lower airways, the lungs and instiltial lung diseases.

TABLE I

Characteristics of Studied Patients with Asthma before Cineol, 4-day Treatment with Cineol 3 × 2 caps./day and 4 Days after Withdrawal of Cineol (Day 8)

| | | | Before Cineol | | 4 Days Cineol | | 4 Days after Cineol | |
|---|---|---|---|---|---|---|---|---|
| Patient | Sex/Age | Corticosteroids | FEV1 (1) | RAW (cm $H_2O/l \cdot s$) | FEV1 (1) | RAW (cm $H_2O/l \cdot s$) | FEV1 (1) | RAW (cm $H_2O/l \cdot s$) |
| 1 | M/42 | | 2.64 | 3.54 | 3.72 | 2.08 | 4.52 | 1.51 |
| 2 | F/56 | Prednisolone 4 mg | 2.2 | 5.67 | 2.6 | 4.22 | 2.04 | 6.17 |
| 3 | F/51 | Prednisone 15 mg | 1.52 | 2.83 | 2.16 | 2.5 | 2.84 | 0.94 |
| 4 | F/65 | Fluocortolone 7.5 mg | 0.76 | 4.94 | 1.48 | 3.92 | 1.4 | 4.19 |
| 5 | F/71 | Prednisolone 4 mg | 2.04 | 5.74 | 2.04 | 3.79 | 1.8 | 3.19 |
| 6 | M/73 | Prednisolone 24 mg | 2.04 | 6.03 | 2.36 | 5.42 | 2.36 | 4.67 |
| 7 | M/51 | Prednisolone 36 mg | 1.28 | 6.4 | 2.0 | 4.85 | 1.96 | 7.8 |
| Mean ± SEM | 58 ± 4 | 13 ± 5 | 1.78 ± 0.24 | 5.02 ± 0.51 | *2.34 ± 0.26 | **3.8 ± 0.45 | †2.4 ± 0.39 | ‡4.06 ± 0.92 |

*p = 0.0273, **p = 0.018, †p = 0.063, ‡= 0.1282

TABLE II

Effects of Long-Term Treatment with Cineol 3 · 2 caps./day in Patients with Asthma

| | Before Cineol | | | | Cineol (3 · 200 mg/day) | | | | |
|---|---|---|---|---|---|---|---|---|---|
| Patient | Corticosteroids (mg/day) | FEV1 (1) | RAW (cm $H_2O/l \cdot s$) | $LTB_4$ (pg/5 · $10^4$) | Time (days) | Corticosteroids (mg/day) | FEV1 (1) | RAW (cm $H_2O/l \cdot s$) | $LTB_4$ (pg/5 · $10^4$) |
| 1 | — | 2.64 | 3.54 | 160.27 | 35 | — | 5.24 | 1.23 | N.A. |
| 2 | 4 | 2.2 | 5.67 | 191.5 | 50 | 2 | 2.2 | 4.78 | 169.8 |
| 3 | 15 | 1.52 | 2.83 | 659.75 | 24 | 5 | 2.36 | 1.94 | 378.52 |
| 4 | 12 | 1.96 | 9.91 | 497.12 | 59 | 8 | 2.04 | 9.3 | N.A. |
| 5 | 7.5 | 0.76 | 4.94 | 156.99 | 26 | 5 | 1.48 | 4.18 | 134.2 |
| 6 | 24 | 2.04 | 6.03 | 125.56 | 67 | 6 | 3.32 | 2.43 | 171 |
| Mean ± | 8.9 | 1.83 | 5.49 | 298.53 | 43.5 | 4.0* | 2.7** | 3.98‡ | 213.38 |
| SEM | 3.3 | 0.26 | 1.02 | 91.38 | 7.3 | 1.3 | 0.55 | 1.2 | 55.7 |

*p = 0.0431, **p = 0.0431, ‡p = 0.0273
N.A. = not analysed

7. The method defined in claim 1 wherein said pharmaceutical compound is used for monotherapy in mild or slight bronchial asthma as well as children's asthma.

8. The method defined in claim 1 wherein said pharmaceutical is used for treatment of autoimmune diseases and to reduce the requirement for immunosuppressants.

9. The method defined in claim 1 wherein said inflammatory disease is an inflammation of the efferent biliary tract.

10. The method defined in claim 9 wherein said inflamation of said efferent biliary tract is cholecystitis.

11. The method defined in claim 9 wherein said inflammation of said efferent biliary tract is cholangitis.

12. The method defined in claim 1 wherein said inflammatory disease is an inflammation of the efferent urinary tract.

13. The method defined in claim 12 wherein said inflammation of said efferent urinary tract is glomerulonephritis.

14. The method defined in claim 12 wherein said inflammation of said efferent urinary tract is pyelonephritis.

15. The method defined in claim 12 wherein said inflammation of said efferent urinary tract is cystitis.

16. The method defined in claim 12 wherein said inflammation of said efferent urinary tract is urethritis.

17. The method defined in claim 1 wherein said inflammation is an inflammation of the arterial and venous vascular system.

18. The method defined in claim 17 wherein said inflammation is arteriosclerosis.

19. The method defined in claim 17 wherein said inflammation is arteriitis.

20. The method defined in claim 17 wherein said inflammation is phlebitis.

21. The method defined in claim 1 wherein said inflammation is inflammatory disease of the intestine.

22. The method defined in claim 1 wherein said inflammation is an inflammation of the articular cartilage in rheumatoid arthritis.

23. The method defined in claim 1 wherein said method is used for purposes of prophylaxis.

24. The method defined in claim 1 wherein said pharmaceutical compound is used in combination with topically or systemically active drugs.

25. The method defined in claim 24 wherein said active drugs are immunosuppressants.

26. The method defined in claim 1 wherein the total daily pharmaceutical intake by said human is between about 100 mg and 900 mg.

27. The method defined in claim 3 wherein the total daily intake of said 1,8-oxido-p-menthane is between about 200 mg and 900 mg.

28. The method defined in claim 27 wherein the total daily intake of said 1,8-oxido-p-menthane is about 600 mg.

29. The method defined in claim 3 wherein the total daily intake of menthane-3-ol is between about 100mg and 450 mg.

30. The method defined in claim 1 wherein said pharmaceutical compound is administered in a dose unit for oral therapy of 100 mg in the form of capsules resistant to gastric juices.

31. The method defined in claim 1 wherein said pharmaceutical administered is added to infusion solutions.

32. The method defined in claim 5 wherein said pharmaceutical compound administered is added to solutions for intramuscular injections.

33. The method defined in claim 1 wherein said inflammatory diseases are diseases of the organs, airways, articular cartilages, arterial and venous vascular system, intestine, the efferent biliary tract and the efferent urinary tract.

34. A method of treating a human to inhibit the onset of a chronic, acute or allergic inflammatory disease comprising:
administering by oral ingestion, infusion solution or intramuscular injection a therapeutically effective amount of a pharmaceutical compound comprising a saturated monocyclic or bicyclic terpene -alcohol, -ether, -ketone, or -thiol,
thereby suppressing the release of arachidonic acid from the phospholipid stores of human cells, and the production and release of inflammatory mediators and cytokines from human cells.

35. A method of treating a human to inhibit the onset of a chronic, acute or allergic inflammatory disease comprising:
systemically administering a therapeutically effective amount of a pharmaceutical compound selected from the group consisting of methane-3-ol and 1,8 cineole,
thereby suppressing the release of arachidonic acid from the phospholipid stores of human cells, and the production and release of inflammatory mediators and cytokines from human cells.

36. A method of treating a human to inhibit the onset of a chronic, acute or allergic inflammatory disease comprising:
systemically administering a therapeutically effective amount of a pharmaceutical compound consisting essentially of a saturated monocyclic or bicyclic terpene -alcohol, -ether, -ketone, or -thiol,
thereby suppressing the release of arachidonic acid from the phospholipid stores of human cells, and the production and release of inflammatory mediators and cytokines from human cells.

37. A method of treating a human to inhibit the onset of a chronic, acute or allergic inflammatory disease comprising:
administering, in the form of a capsule resistant to gastric juice, a therapeutically effective amount of a pharmaceutical compound comprising a saturated monocyclic or bicyclic terpene -alcohol, -ether, -ketone, or -thiol,
thereby suppressing the release of arachidonic acid from the phospholipid stores of human cells, and the production and release of inflammatory mediators and cytokines from human cells.

38. A method of reducing the steroid requirement in the treatment of an inflammatory disease treated with a corticosteroid comprising: systemically administering a therapeutically effective amount of a pharmaceutical compound comprising a saturated monocyclic or bicyclic terpene -alcohol, -ether, -ketone, or -thiol.

39. A method of treating a human having an inflammatory condition which is bronchial asthma comprising: administering to said patient by a capsule resistant to gastric juices, infusion solution or intramuscular injection, a therapeutically effective amount of 1,8-cineole or menthane-3-ol.

* * * * *